US009389170B2

(12) United States Patent
Moy et al.

(10) Patent No.: US 9,389,170 B2
(45) Date of Patent: *Jul. 12, 2016

(54) DEVICE FOR MEASURING LIQUID PROPERTY

(71) Applicant: AXALTA COATING SYSTEMS IP CO., LLC, Wilmington, DE (US)

(72) Inventors: Anthony Moy, Waxhaw, NC (US); Ayumu Yokoyama, Media, PA (US); Allan Blase Joseph Rodrigues, Bloomfield Hills, MI (US); Ken Stephen Schermacher, Chadds Ford, PA (US); Jeff B. Alspach, Lake Orion, MI (US)

(73) Assignee: AXALTA COATING SYSTEMS IP CO., LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/412,832

(22) PCT Filed: May 15, 2013

(86) PCT No.: PCT/US2013/041051
§ 371 (c)(1),
(2) Date: Jan. 5, 2015

(87) PCT Pub. No.: WO2014/014555
PCT Pub. Date: Jan. 23, 2014

(65) Prior Publication Data
US 2015/0160123 A1    Jun. 11, 2015

Related U.S. Application Data

(60) Provisional application No. 61/672,461, filed on Jul. 17, 2012.

(51) Int. Cl.
G01J 3/46     (2006.01)
G01N 21/25    (2006.01)
G01N 33/32    (2006.01)
G01N 21/84    (2006.01)
G01N 1/28     (2006.01)

(52) U.S. Cl.
CPC ............ G01N 21/251 (2013.01); G01N 1/2813 (2013.01); G01N 21/8422 (2013.01); G01N 33/32 (2013.01); G01N 2201/02 (2013.01)

(58) Field of Classification Search
CPC ................. G01J 3/02; G01J 3/46; G01J 3/50; G01J 3/51; G01J 3/52; G01N 21/27; G01N 33/32; G01N 1/28
USPC .................................................. 356/402–425
See application file for complete search history.

(56) References Cited

U.S. PATENT DOCUMENTS 6,091,914 A    7/2000  Yoo
6,583,878 B2   6/2003  Hustert
(Continued)

FOREIGN PATENT DOCUMENTS

DE       2525701 A1    12/1976
WO    2012051290 A2     4/2012

OTHER PUBLICATIONS

ISA KIPO, International Search Report for International Application No. PCT/US2013/041051, dated Sep. 11, 2013.

Primary Examiner — Abdullahi Nur
(74) Attorney, Agent, or Firm — Ingrassia Fisher & Lorenz, P.C.

(57) ABSTRACT

A liquid measuring system for producing one or more property values of a liquid. The system can include: a thin film device and one or more measuring devices for measuring said one or more property values. The system includes a thin film device for producing a thin film of the liquid on a spinning disk. The system is particularly useful for measuring color and appearance properties of the liquid. The system can be useful for producing coating compositions.

20 Claims, 12 Drawing Sheets

(56) References Cited

U.S. PATENT DOCUMENTS

2002/0167663 A1 11/2002 Martino et al.
2003/0004229 A1 1/2003 Schermacher et al.
2015/0160122 A1* 6/2015 Moy .................... G01N 21/251
 73/150 R

* cited by examiner

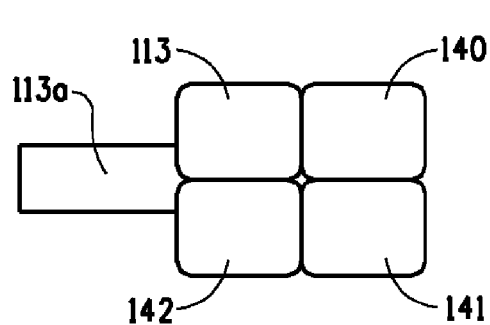
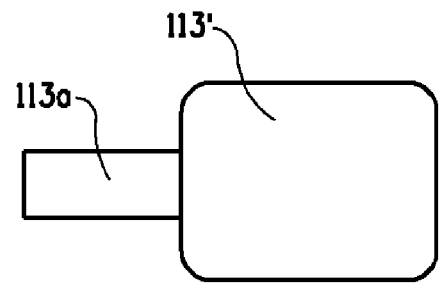
FIG. 5A          FIG. 5B
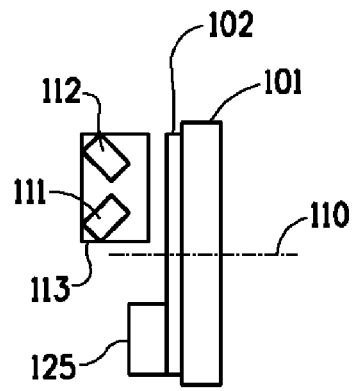
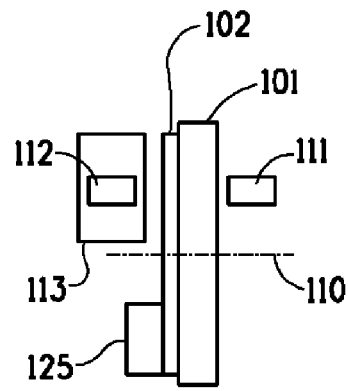
FIG. 6A          FIG. 6B
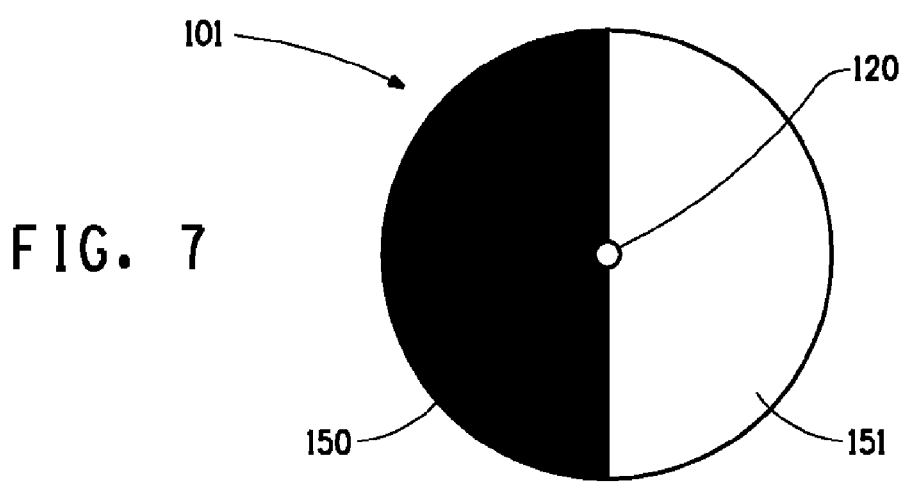
FIG. 7

DEVICE FOR MEASURING LIQUID PROPERTY

CROSS-REFERENCE TO RELATED APPLICATION

This application is a U.S. National-Stage entry under 35 U.S.C. §371 based on International Application No. PCT/US2013/041051, filed May 15, 2013, which was published under PCT Article 21(2) and which claims priority to U.S. Provisional Application No. 61/672,461, filed Jul. 17, 2012, which are all hereby incorporated in their entirety by reference.

TECHNICAL FIELD

The technical field generally relates to a thin film device and a liquid measuring system for producing one or more property values of a liquid. The disclosure is particularly directed to a thin film device and a system for measuring color and other properties of a wet thin film of a liquid.

BACKGROUND

Compositions such as inks and coating compositions can be typically produced in liquid forms and can be produce into dry forms for industrial or consumer applications, such as printed materials or coatings on vehicles, appliances, or buildings. Production of such compositions can involve complex processes. The composition can have a plurality of properties including wet properties such as pH, viscosity, or wet color; and dry properties such as hardness or dry color. Typically, some of the wet properties can be different from the dry properties for the same composition. For example, wet color of a coating composition can be different from dry color of the same coating composition after cured or otherwise dried.

Currently, in order to produce a composition having desired dry properties, repeated tries and adjustments can be involved and can include the steps of producing an intermediate of the composition, drying it to form a dried composition, measuring dry properties of the dried composition, adjusting the composition, and repeat again until the desired properties are achieved. Such process is time and effort consuming and leads to time delays in production. For example, a coating composition batch can stay in a mixing tank for an extended time period while tests are run in control labs for producing dry samples to test coating properties.

Thus, needs exist for improved devices and processes to produce one or more property values of a liquid when it is wet.

SUMMARY

A thin film device for producing a thin film of a liquid is provided for. The thin film device comprises:

a disk comprising a planar first surface and a second disk surface on the opposite sides of said disk, said disk is coupled to a rotation shaft that is aligned with a rotational axis of the disk perpendicular to the disk surfaces for providing rotation to the disk along said rotational axis;

a device frame that positions said rotation shaft and said disk;

a thickness control device comprising a thin film setting edge coupled to a liquid return channel and at least one frame connector coupling said thin film setting edge and said liquid return channel to said device frame, said frame connector is movable in respect to said device frame; and a motion device coupled to said rotation shaft for providing rotation to the rotation shaft, and a motion control device for controlling rotation speed, rotation direction, or a combination thereof, of said motion device;

wherein said thickness control device is positioned at said planar first surface side of said disk, and said thin film setting edge is substantially parallel to said planar first surface, and said thin film setting edge overlaps with said disk covering in a range of from about 50% to about 99% of the radius of said disk; and wherein the distance between said thin film setting edge and said planar first surface is in a range of from about 0.05 mm to about 5 mm and adjustable via said frame connector.

A liquid measuring system for producing one or more property values of a liquid is provided for. The liquid measuring system comprises:

the thin film device disclosed herein; and one or more measuring devices for measuring said one or more property values.

A kit for assembling into the thin film device disclosed herein is also provided.

BRIEF DESCRIPTION OF DRAWING

The various embodiments will hereinafter be described in conjunction with the following drawing figures, wherein like numerals denote like elements, and:

(FIG. 1A) a thin film device having a dipping reservoir, (FIG. 1B) a thin film device having a cup reservoir, (FIG. 1C) an example of a disk having a second surface protruding from the disk and (FIG. 1D) an example of a disk having a second surface recessing into the disk.

(FIG. 2A) a thin film device having a dipping reservoir, (FIG. 2B) a thin film device having a cup reservoir and (FIG. 2C) a thin film device having a recessing second surface.

(FIG. 3A) a thin film device having a dipping reservoir and (FIG. 3B) a thin film device having a cup reservoir.

FIGS. A5 through 5B show examples of configurations of measuring devices: (FIG. 5A) an example of a configuration for one or more measuring devices and (FIG. 5B) an example of a configuration for a device having one or more measuring functions.

FIGS. 6A through 6B show top-down views of schematic diagrams of a part of examples of the thin film device: (FIG. 6A) with an illumination device and a detection device on the same side of the disk; and (FIG. 6B) with an illumination device and a detection device on opposite sides of the disk.

FIG. 7 shows an example of a disk having a hiding pattern thereon.

DETAILED DESCRIPTION

Figure 1A:
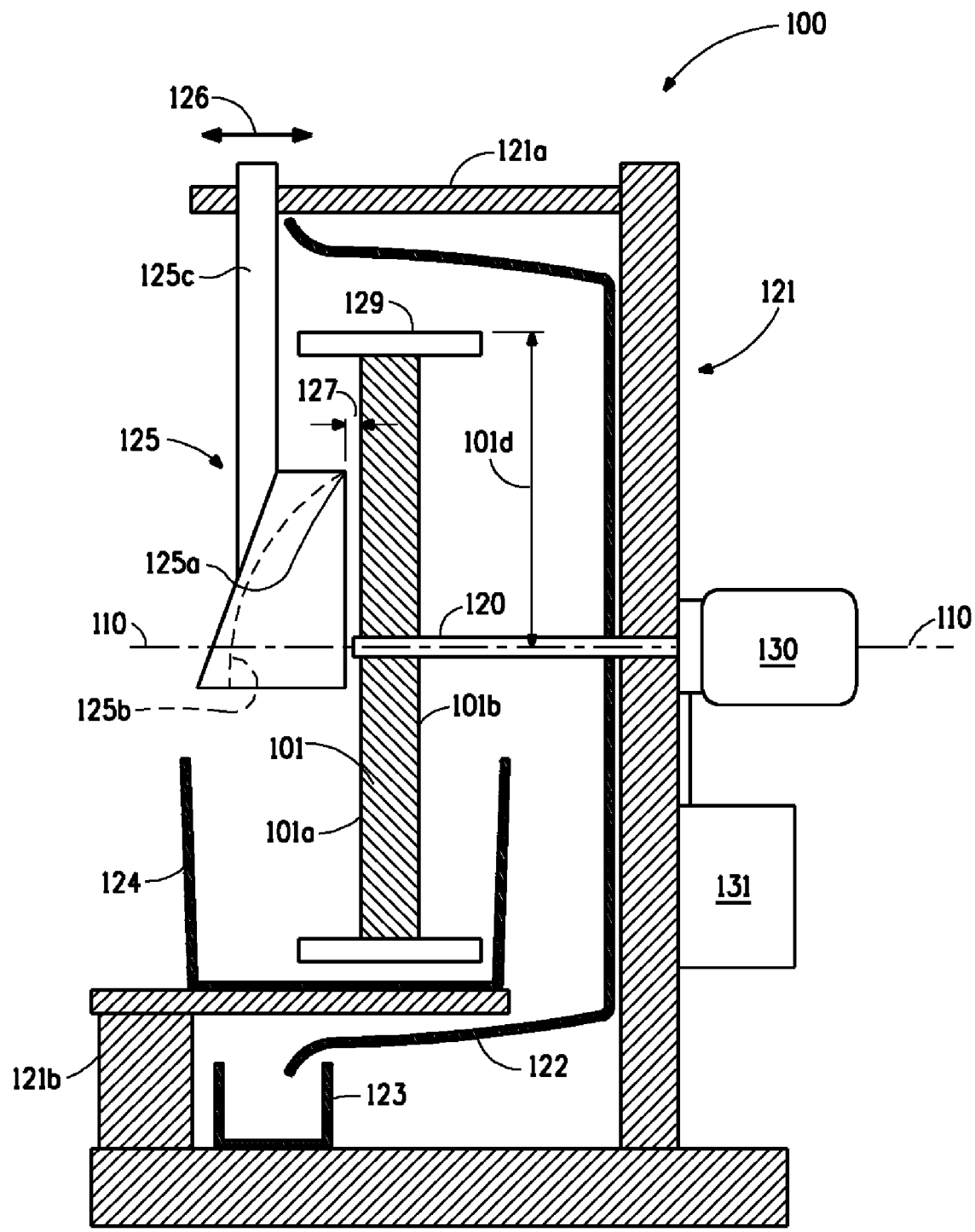
FIGS. 1A through 1D show side cross-sectional schematic diagrams of examples of the thin film device.

The following detailed description is merely exemplary in nature and is not intended to limit the exemplary embodiments or the application and uses of the exemplary embodiments. Furthermore, there is no intention to be bound by any theory presented in the preceding background or the following detailed description.

The features and advantages of the exemplary embodiments will be more readily understood, by those of ordinary skill in the art, from reading the following detailed description. It is to be appreciated that certain features of the exemplary embodiments, which are, for clarity, described above and below in the context of separate embodiments, may also be provided in combination in a single embodiment. Conversely, various features of the exemplary embodiments that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

A computing device used herein can refer to a data processing chip, a desktop computer, a laptop computer, a pocket PC, a personal digital assistant (PDA), a handheld electronic processing device, a smart phone that combines the functionality of a PDA and a mobile phone, or any other electronic devices that can process information automatically. A computing device can be built into other electronic devices, such as a built-in data processing chip integrated into an imaging device, color measuring device, or an appearance measuring device. A computing device can have one or more wired or wireless connections to a database, to another computing device, or a combination thereof. A computing device can be a client computer that communicates with a host computer in a multi-computer client-host system connected via a wired or wireless network including intranet and internet. A computing device can also be configured to be coupled with a data input or output device via wired or wireless connections. For example, a laptop computer can have data input devices such as key board, USB connections, or a touch screen and can be operatively configured to receive data and images through wired or wireless connections. A "portable computing device" can include a laptop computer, a pocket PC, a personal digital assistant (PDA), a handheld electronic processing device, a mobile phone, a smart phone, a tablet computer, or any other electronic devices that can process information and data and can be carried by a person.

Wired connections can include hardware couplings, splitters, adaptors, connectors, cables or wires. Wireless connections and devices can include, but not limited to, Wi-Fi device, Bluetooth device, wide area network (WAN) wireless device, local area network (LAN) device, infrared communication device, optical data transfer device, radio transmitter and optionally receiver, wireless phone, wireless phone adaptor card, or any other devices that can transmit signals in a wide range of radio frequency including visible or invisible optical wavelengths and electromagnetic wavelengths.

The term "wet" refers to a state of being liquid that is able to flow or adapt into a shape, such as the shape of a container or a substrate. Examples of wet compositions can include wet inks that have not dried or cured or wet coating compositions that have not dried or cured. A wet coating composition can be in a storage container or over a coated substrate and can adapt to the shape of the container or the shape of the substrate. A wet coating composition can comprise one or more liquid solvents, such as water, one or more organic solvents, one or more inorganic solvents, or a combination thereof. The "wet" property values refer to the property associated with a composition values when the composition is being wet. A wet coating composition refers to a film or surface of the coating composition that is wet and not dry to be touched as determined by ASTM D1640.

The term "database" refers to a collection of related information that can be searched and retrieved. The database can be a searchable electronic numerical or textual document, a searchable PDF document, a Microsoft Excel® spreadsheet, an Microsoft Access® database (both supplied by Microsoft Corporation of Redmond, Wash.), an Oracle® database (supplied by Oracle Corporation of Redwood Shores, Calif.), or a Lynux database, each registered under their respective trademarks. The database can be a set of electronic documents, photographs, images, diagrams, or drawings, residing in one or more computer readable storage media that can be searched and retrieved. A database can be a single database or a set of related databases or a group of unrelated databases. "Related database" means that there is at least one common information element in the related databases that can be used to relate such databases. One example of the related databases can be Oracle® relational databases.

"Appearance" used herein refers to (1) the aspect of visual experience by which a coating or an object is viewed or recognized; and (2) perception in which the spectral and geometric aspects of a coating or an object is integrated with its illuminating and viewing environment. In general, appearance can include shape, texture, sparkle, glitter, gloss, transparency, color, opacity, other visual effects of a coating or an object, or a combination thereof. Appearance can vary with varying viewing angles or varying illumination angles.

Color data can be selected from or include L,a,b color values, L*,a*,b* color values, XYZ color values, L,C,h color values, spectral reflectance values, light absorption (K) and scattering (S) values (also known as "K,S values"), or a combination thereof, and can be stored in and retrieved from one or more databases. Other color values such as Hunter Lab color values, ANLAB color values, CIE LAB color values, CIE LUV color values, L*,C*,H* color values, any other color values known to or developed by those skilled in the art, or a combination thereof, can also be used.

This disclosure is directed to a thin film device (100) for producing a thin film (102) of a liquid. The thin film device can comprise:

(a) a disk (101) comprising a planar first surface (101a) and a second disk surface (101b) on the opposite sides of said disk, said disk is coupled to a rotation shaft (120) that is aligned with a rotational axis (110) of the disk perpendicular to the disk surfaces for providing rotation to the disk along said rotational axis (110);

(b) a device frame (121) that positions said rotation shaft and said disk;

(c) a thickness control device (125) comprising a thin film setting edge (125a) coupled to a liquid return channel (125b) and at least one frame connector (125c) coupling said thin film setting edge (125a) and said liquid return channel (125b)

to said device frame (121), said frame connector is movable in respect to said device frame; and (d) a motion device (130) coupled to said rotation shaft for providing rotation to the rotation shaft (120), and a motion control device (131) for controlling rotation speed, rotation direction, or a combination thereof, of said motion device;

wherein said thickness control device (125) is positioned at said planar first surface (101a) side of said disk (101), said thin film setting edge (125a) is substantially parallel to said planar first surface, and said thin film setting edge (125a) overlaps with said disk covering in a range of from about 50% to about 99% of the radius of said disk (101); and wherein the distance (127) between said thin film setting edge (125a) and said planar first surface (101a) is in a range of from about 0.05 mm to about 5 mm and adjustable via said frame connector.

In another embodiment, the thin film device can comprise:

(a) a disk (101) comprising a planar first surface (101a) and a second disk surface (101b) on the opposite sides of said disk, said disk is coupled to a rotation shaft (120) that is aligned with a rotational axis (110) of said disk perpendicular to the planar first surface allowing rotation of the disk along said rotational axis (110), at least a circular portion (101e) of said planar first surface is rotationally symmetric to said rotational axis;

(b) a device frame (121) that positions said rotation shaft and said disk;

(c) a thickness control device (125) comprising a thin film setting edge (125a) coupled to a liquid return channel (125b) and at least one frame connector (125c) coupling said thin film setting edge (125a) and said liquid return channel (125b) to said device frame (121), said frame connector is movable in respect to said device frame; and (d) a motion device (130) coupled to said disk for providing rotation to the disk, and a motion control device (131) for controlling rotation speed, rotation direction, or a combination thereof, of said motion device;

wherein said thickness control device (125) is positioned at said planar first surface (101a) side of said disk (101), and said thin film setting edge (125a) is substantially parallel to said planar first surface; and wherein the distance (127) between said thin film setting edge (125a) and said planar first surface (101a) is in a range of from about 0.05 mm to about 5 mm and adjustable via said frame connector.

The thin film can be wet as defined above.

Figure 1B:
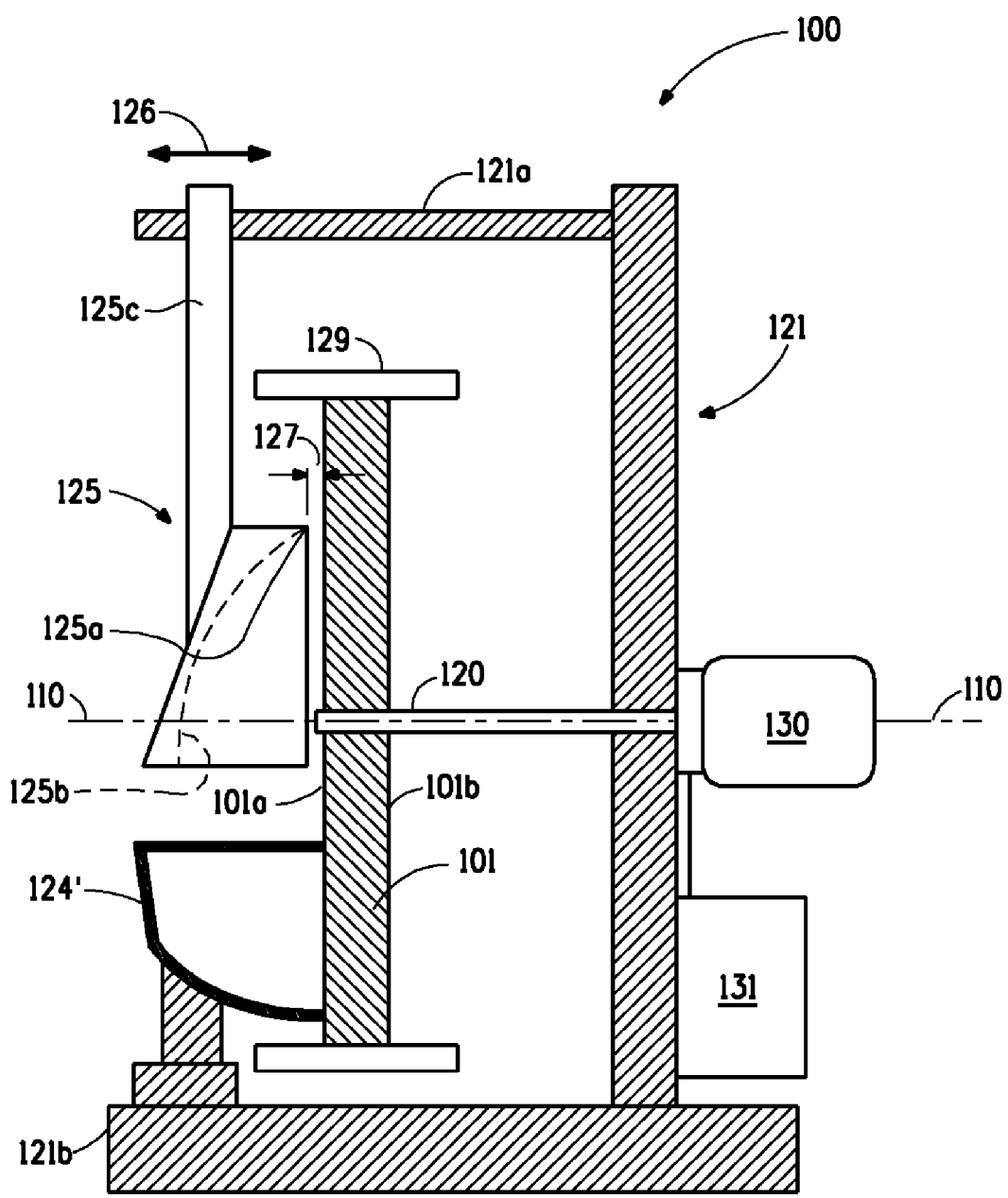

Examples of the thin film device can include the ones shown in FIG. 1A and FIG. 1B. The disk can be non-transparent or transparent.

Figure 1C:
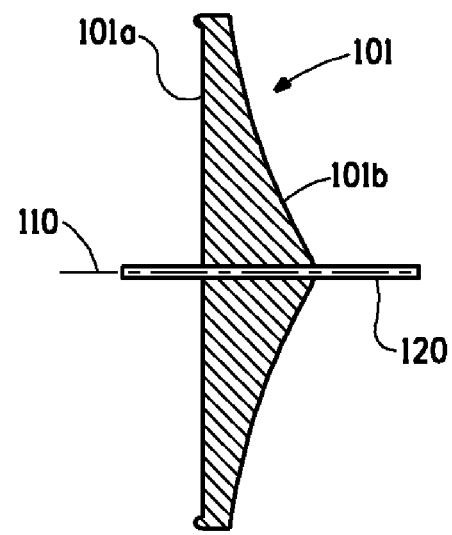
Figure 1D:
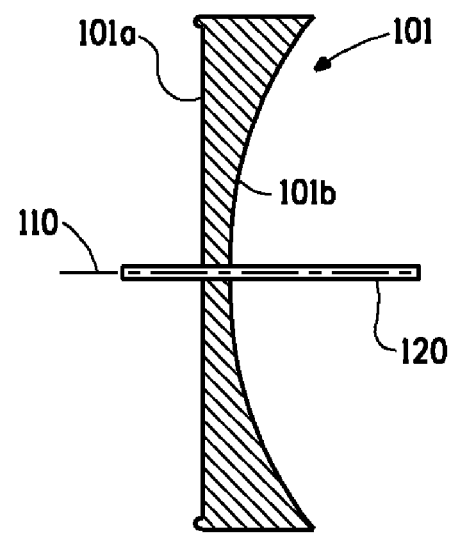
Figure 2A:
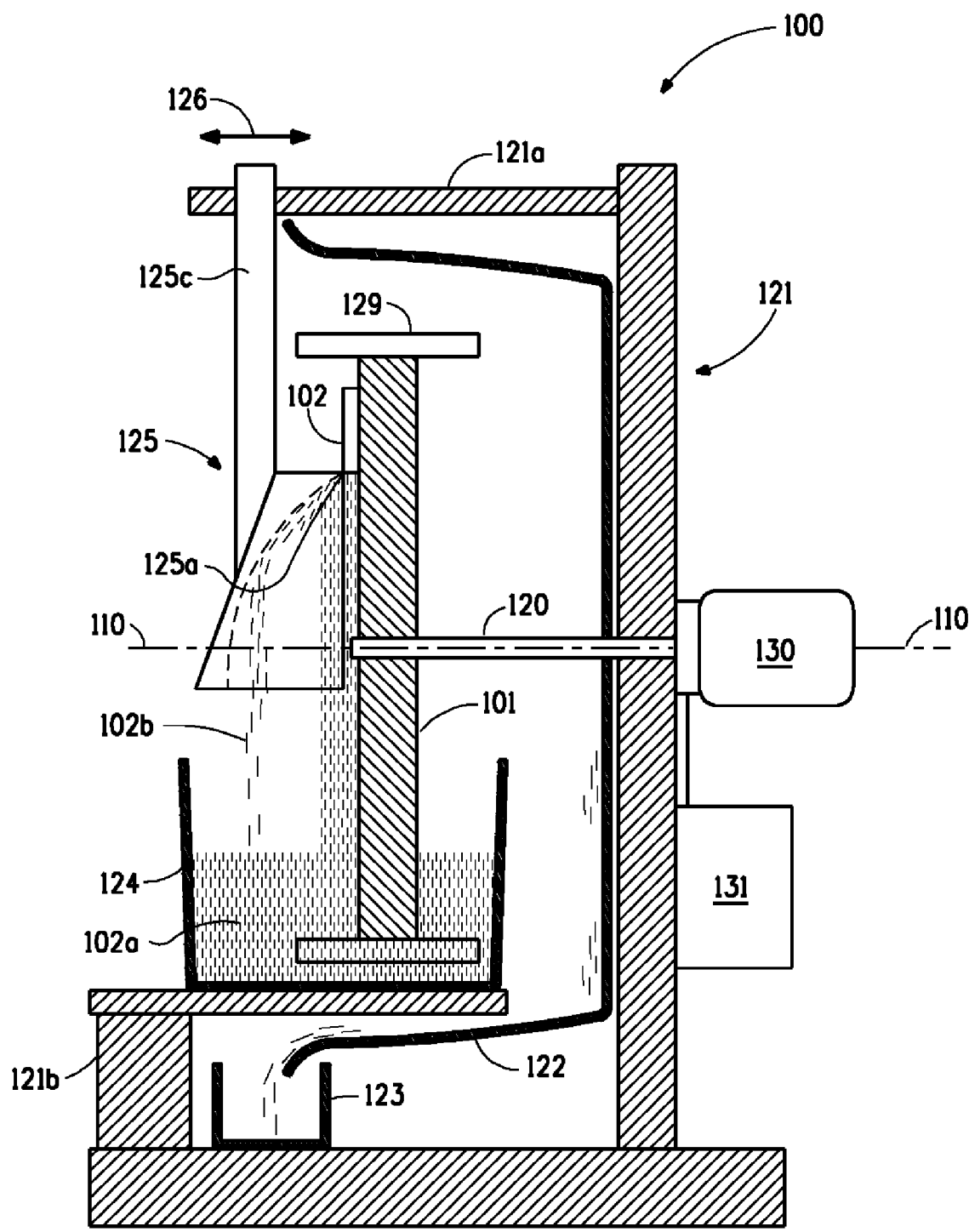
FIGS. 2A through 2C show side cross-sectional schematic diagrams of examples of the thin film device with the liquid on the planar first surface.
Figure 2B:
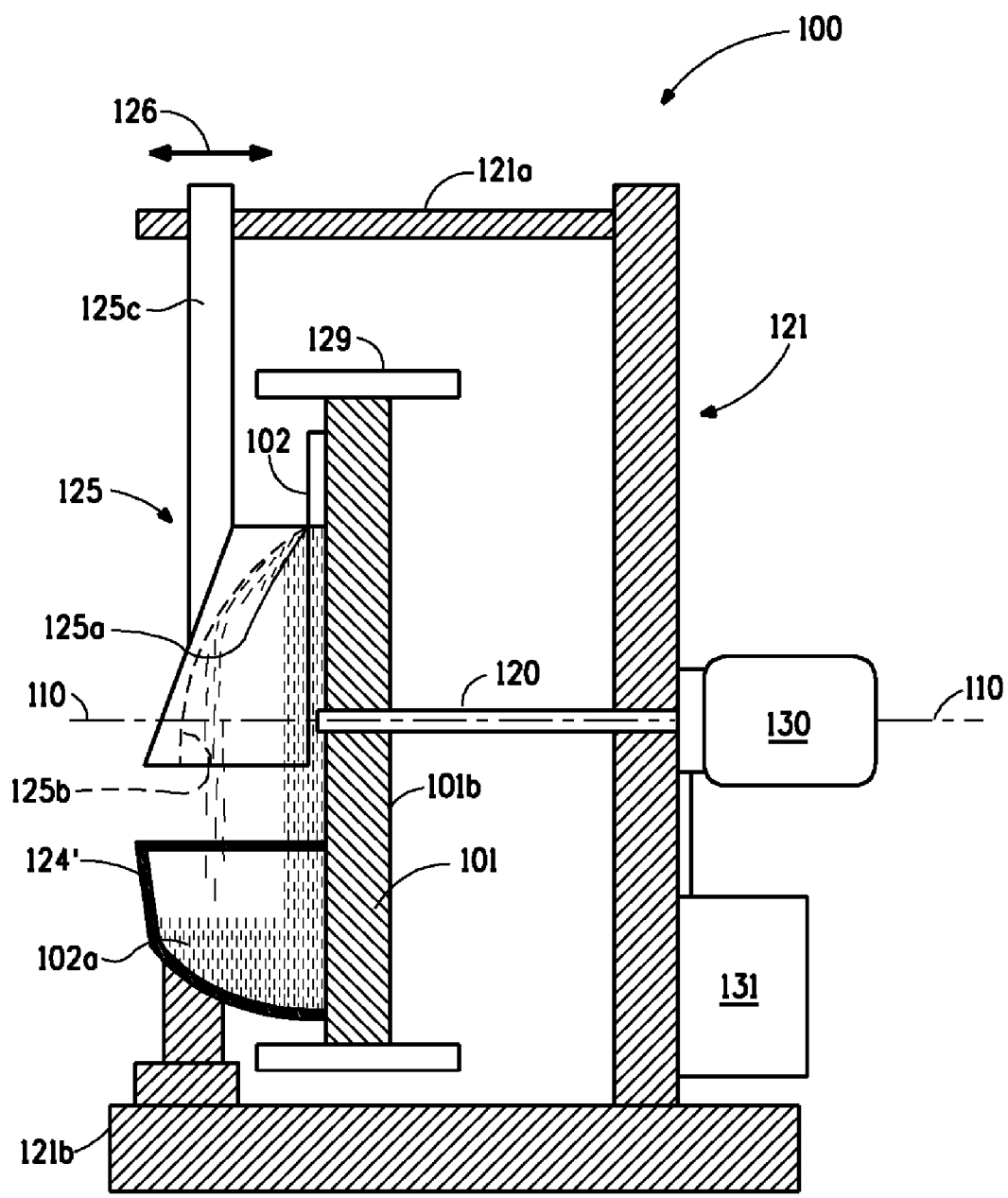
Figure 2C:
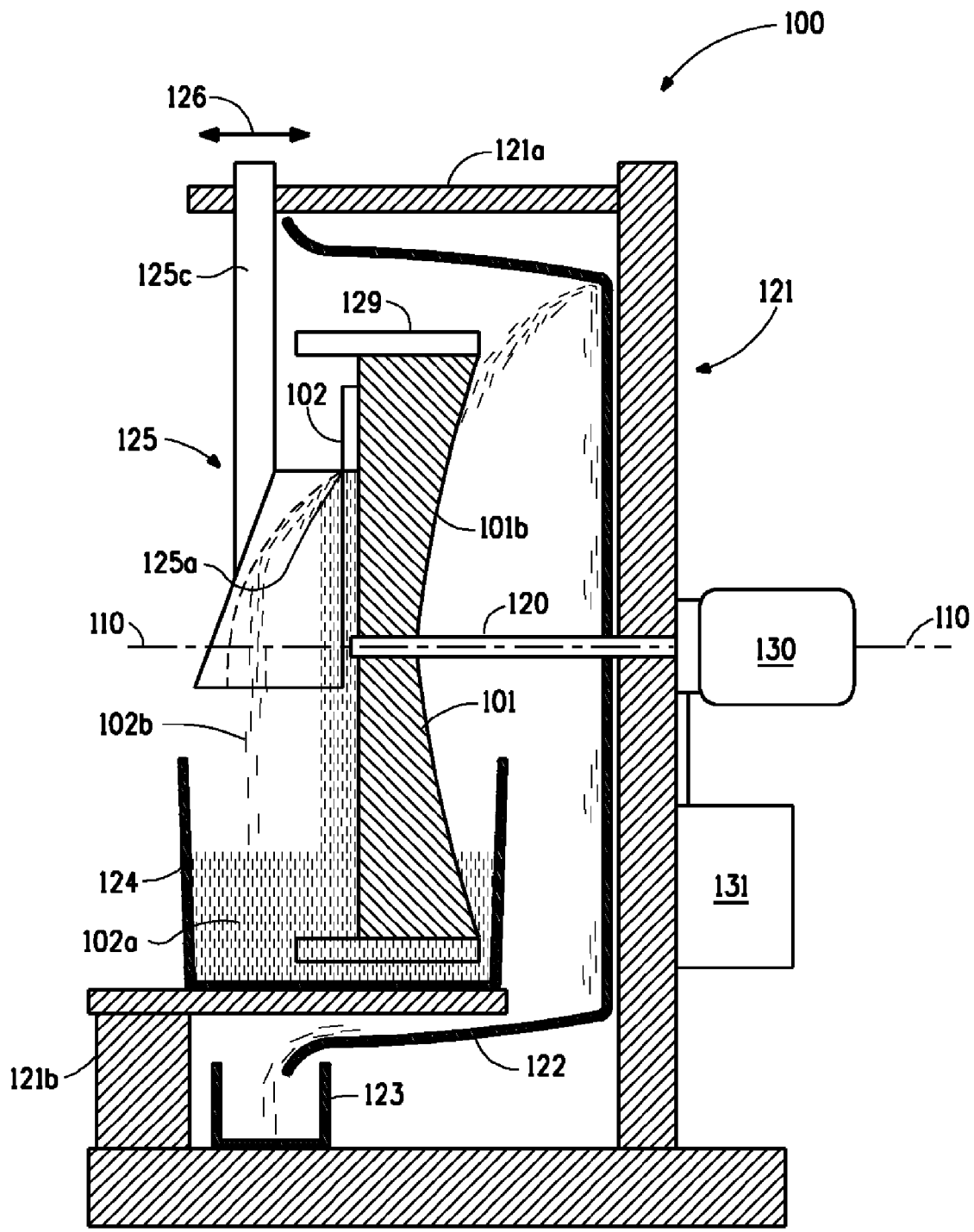

The second disk surface (101b) can be a non-planar surface, such as a surface protruding from the disk (FIG. 1C) or a surface recessing into the disk (FIG. 1D). The surface protruding from the disk can be beneficial, such as providing better stability to the disk, especially when the disk is very thin in thickness. The surface recessing into the disk can also be beneficial, such as for easy discharging of excess liquid to a retainer described herein when the disk is in rotation, such as shown in FIG. 2C.

The thin film device can further comprise a first reservoir (124) for storing said liquid (102a) (FIG. 1A-1B and FIG. 2A-2C). The first reservoir can be configured so that the liquid, when present in the first reservoir, is in contact with at least a portion of the planar first surface. The first reservoir can be a dip reservoir (124), such as the one shown in FIG. 1A, or a cup reservoir (124'), such as the one shown in FIG. 1B. The dip reservoir can have a portion of the disk dipped within so the liquid, when present, can be in contact with the planar first surface and the second surface in the reservoir. The cup reservoir can provide the liquid to be in contact with only one of the surfaces, such as the planar first surface only. In one example, the cup reservoir can have a side opening to allow the liquid in the reservoir, when present, to be in contact with the planar first surface, and a top opening to allow the liquid, when present, to flow on the planar first surface from the reservoir to the thin film setting edge, while side walls and bottom walls of the cup reservoir can be in contact with the planar first surface to hold the liquid, when present, in the reservoir.

The thin film device can further comprise a second reservoir (123) and a retainer (122). The second reservoir can be positioned to collect overflow of the liquid, when present, retained by the retainer (122) (FIG. 2A and FIG. 2C). The retainer can be affixed to the device frame (121). The device frame (121) can have a frame base (121b) that can have one or more tiers for positioning the first and the second reservoirs.

Figure 3A:
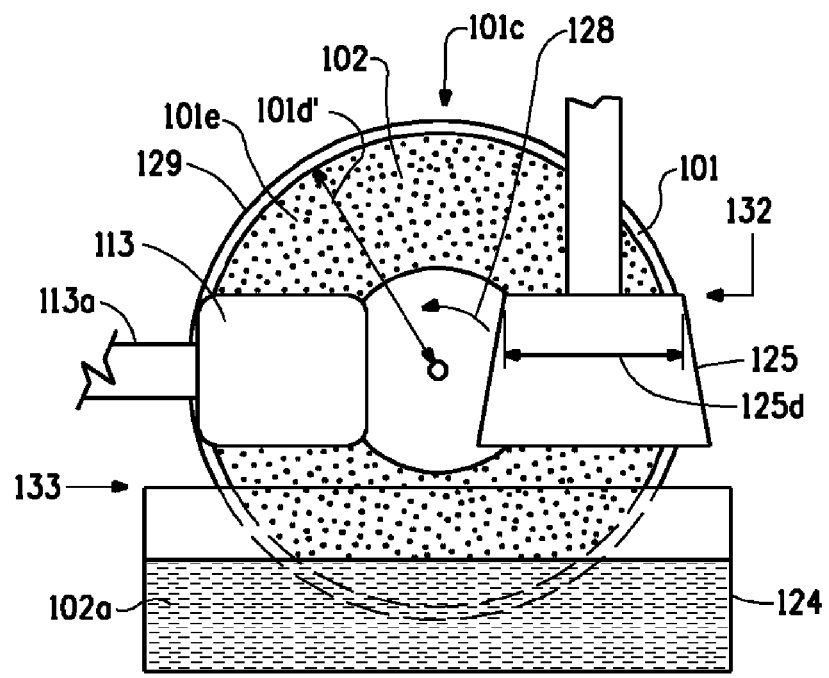
FIGS. 3A through 3B show frontal views of schematic diagrams of examples of the thin film device.
Figure 3B:
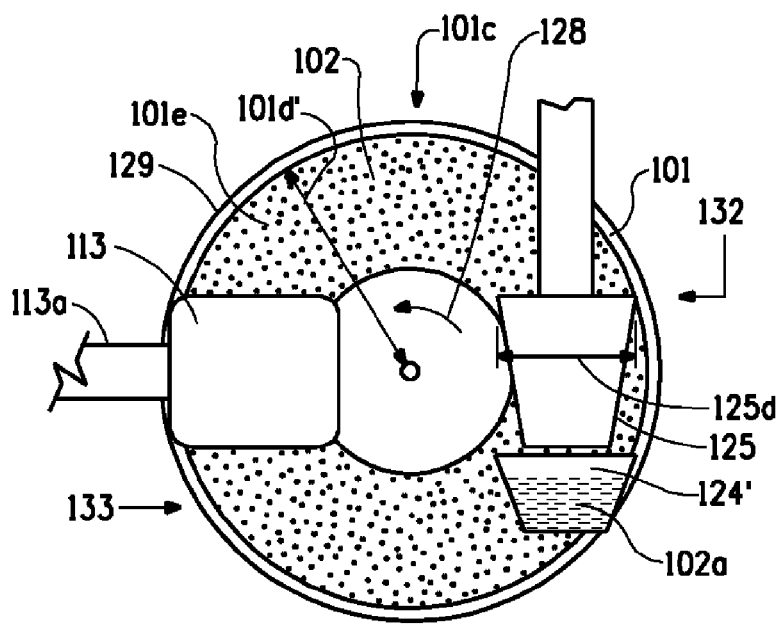

The disk (101) can be a circular disk and can further comprise a circular retaining barrier (129) positioned at the circular edge of the disk. The circular retaining barrier can be a belt around the edge of the disk, a circular grove or a curved edge, a protruding around the edge of the disk, or a combination thereof. A non-circular disk can also be suitable when the non-circular disk has at least a circular portion (101e) (FIG. 3A-3B) of the planar first surface that is rotationally symmetric to the rotational axis. The thin film (102) can be formed on the circular portion (101e).

The disk (101) can be so positioned that the liquid, when present, can be moved by the disk, when in rotation, from the first reservoir to the thin film setting edge against gravity. The planar first surface can be made of stainless steel, polymers, plastics, glass, or a combination thereof. The planar first surface should be suitable for forming a thin film of said liquid thereon having essentially even thickness for at least a portion of the planar first surface large enough for measuring properties of the liquid.

The thickness control device can be constructed from plastics, metals, glass, other suitable materials, or a combination thereof. Typically, all parts of the thin film device can be made from materials that are not reactive to the liquid. In one example, the thin film setting edge (125a) and the liquid return channel (125b) can be molded from plastic materials and coupled to at least one frame connector (125c). In another example, the thin film setting edge and the liquid return channel can be constructed from the same or different materials and assembled together and then coupled to at least one frame connector. The liquid return channel can be configured to have a shape that allows the liquid to return to the first reservoir by gravity without disturbing the thin film formed. It is preferred that the liquid return channel is positioned below the thin film setting edge and above the first reservoir to return excess liquid, when present, via gravity.

The thin film setting edge and the liquid return channel can be coupled to one or more frame connectors. The one or more frame connectors can be coupled to the device frame via one or more frame couplings (121a) and can be moved in adjustment directions (126) to adjust the distance (127) between the thin film setting edge and the planar first surface (FIG. 1A-1B). The thin film setting edge can be in a strait linear configuration, a non-linear or curved configuration, as long as the distance between the thin film setting edge and the planar first surface is essentially the same along the edge and is in the range required herein so a thin film of the liquid having an essentially even thickness can be formed on the planar first surface. Being "essentially", the distance between the thin film setting edge and the planar first surface can have small variations, typically less than about 20% variations of the average distance. In one example, when a desired distance is about 0.5 mm, the actual distance can be, along the edge of the thin film setting edge, in a range of from about 0.4 mm to about 0.6 mm.

The length (125d) of the thin film setting edge (125a) can be in a range of from about 50% to about 99% of the radius (101d) of the disk. Typically, the thickness control device can be positioned within a projected space of the disk. The projected space is the space encircled by the imaginary boundary projected from the edge of the disk towards either sides of the disk parallel to the aforementioned rotational axis (110). The thickness control device can also be positioned beyond the projected space of the disk, especially when the disk is free from a protruding edge. In one example, the thickness control device is positioned so the thin film setting edge is positioned horizontally. In another example, the thickness control device is positioned so the thin film setting edge is positioned vertically. In yet another example, the thickness control device is positioned so the thin film setting edge is positioned at an angle between about 0° (horizontally) and about 90° (vertically).

The thin film setting edge (125a) can overlap with the disk covering in a range of from about 50% to about 120% of the radius (101d') of the circular portion of the planar first surface. Typically, the circular portion of the planar first surface can cover part or entire surface of the disk. The radius (101d') of the circular portion of the planar first surface can be in a range of from about 50% to about 100% in one example, about 50% to about 99% in another example, about 50% to about 90% in yet another example, about 50% to about 80% in yet another example, of the radius (101d) of the disk.

Figure 4A:
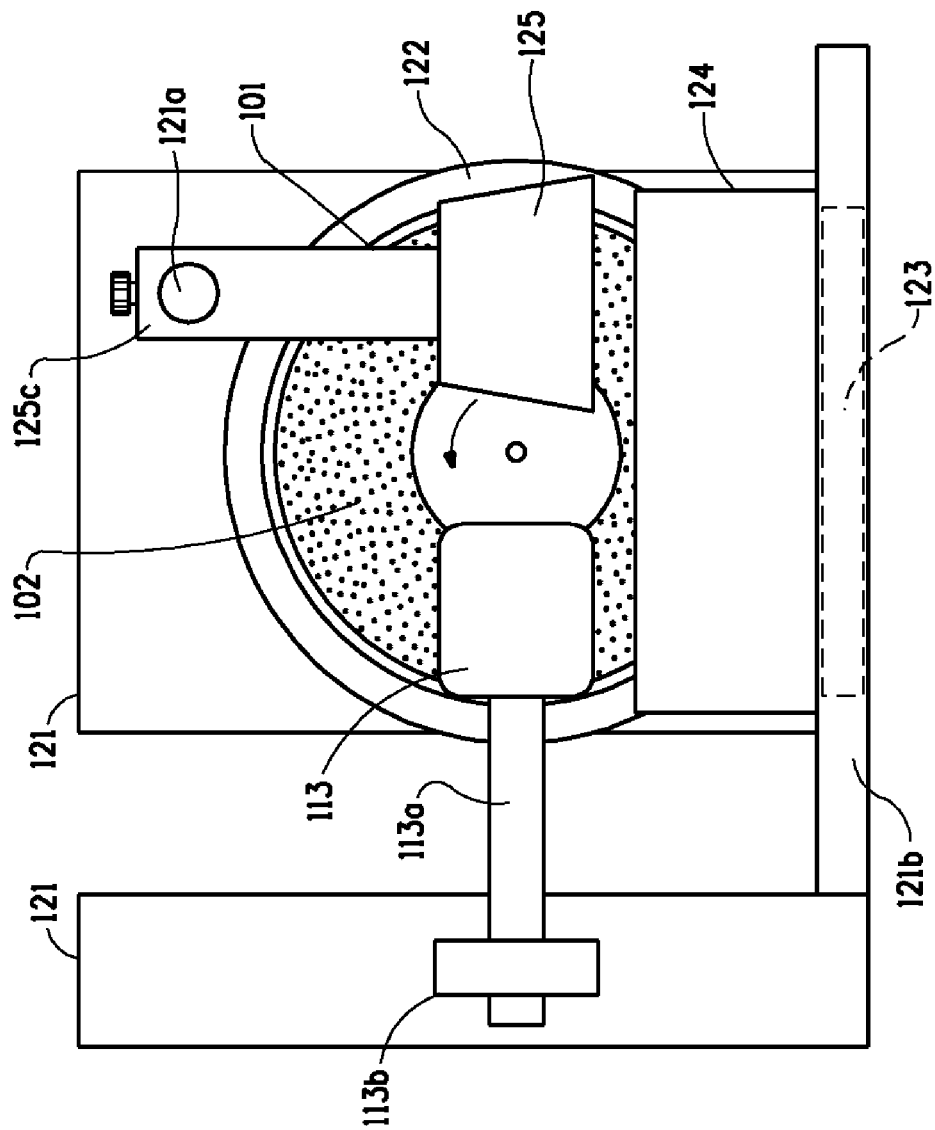
FIGS. 4A through 4E show a side view of a schematic diagram of (FIG. 4A) an example of a system having the frame connector configured vertically, (FIG. 4B) an example of a system having the frame connector configured horizontally, (FIG. 4C) an example of a motion transfer device having a belt coupling to the disk and the motion device, (FIG. 4D) an example of a motion transfer device having a belt or chain coupling the edge of the disk and the motion device, and (FIG. 4E) an example of a motion transfer device having a wheel in contact with the disk for transfer motion from the motion device to the disk.
Figure 4B:
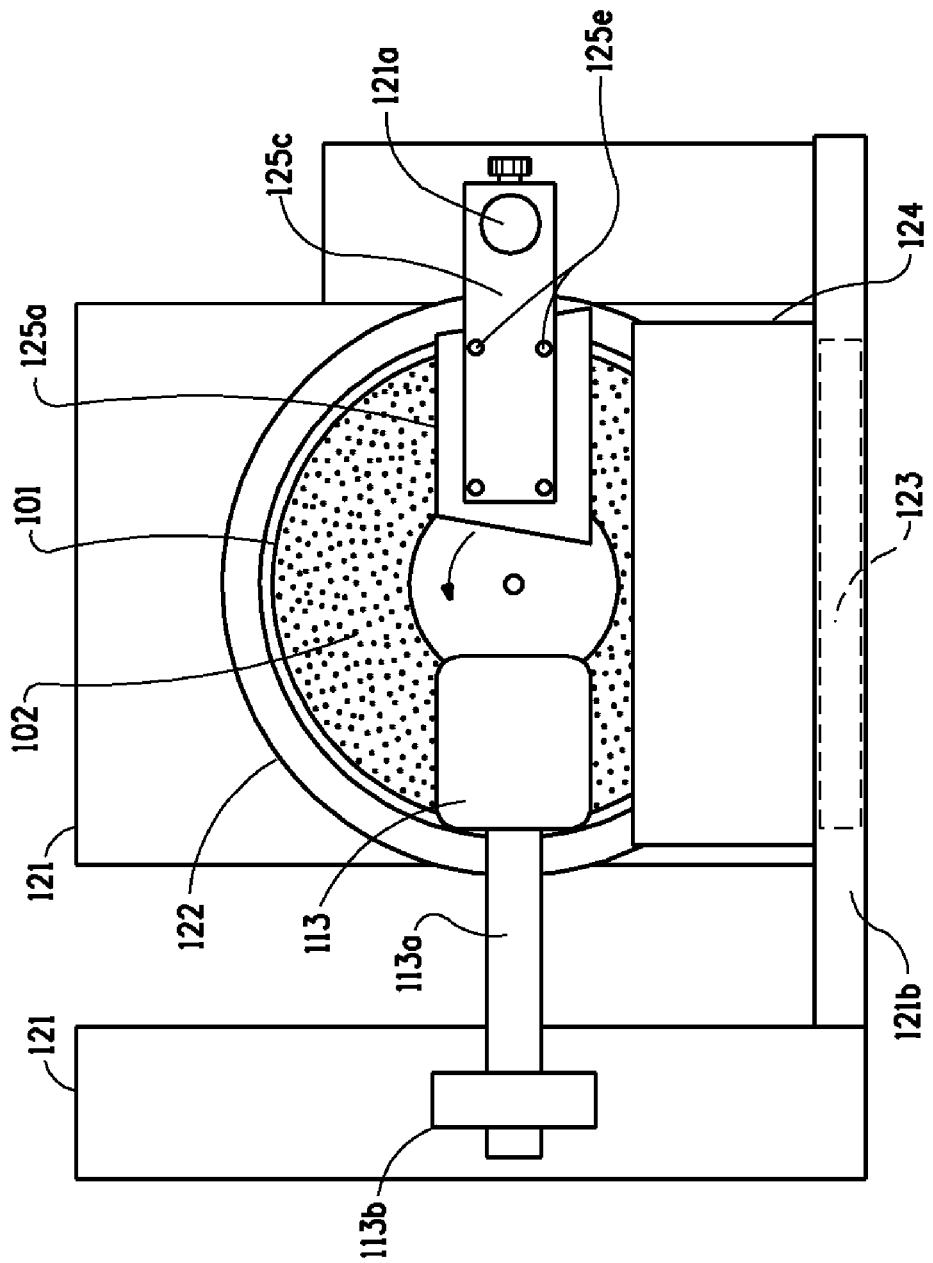

The thickness control device (125) can have the frame connector configured vertically (FIG. 4A) or horizontally (FIG. 4B). The thickness control device can further comprise one or more thickness adjusters (125e) that can adjust the distance between the thin film setting edge and the planar first surface, the position of the thin film setting edge, the angle of the thin film setting edge, the angle of the liquid return channel, or a combination thereof. The one or more thickness adjusters (125e) can be combined with the frame connectors configured vertically (FIG. 4A) or horizontally (FIG. 4B).

Figure 4C:
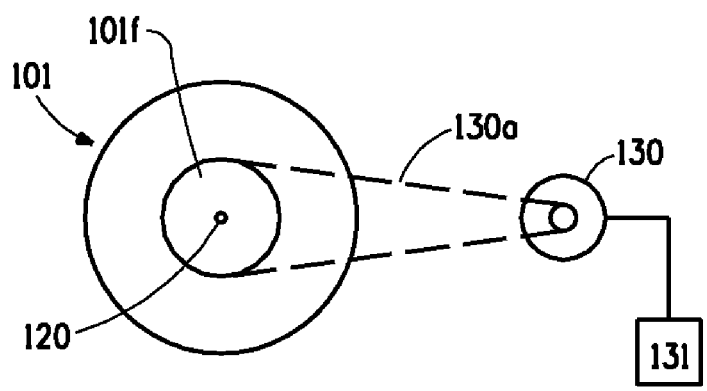
Figure 4D:
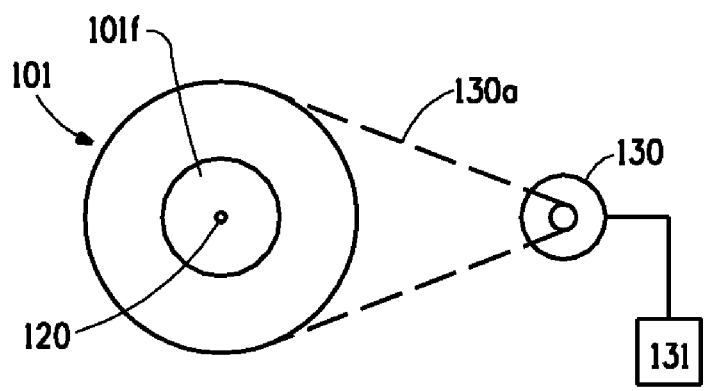

The motion device (130) can be coupled to the disk by directly coupling to the rotation shaft (120), via a motion transfer device, or a combination thereof. In one example, the motion device can be directly coupled to the rotation shaft, such as shown on FIG. 1A-1B and FIG. 2A-2C. In another example, the motion device can be coupled to the disk via a motion transfer device. The motion transfer device can comprise a motion coupler (101f) coupled to the disk (101) and a circular belt or chain (130a). The circular belt or chain (130a) can be coupled to the motion coupler (101f) or the disk to transfer the motion from the motion device to the disk causing the disk to rotate. Schematic representations are shown in FIG. 4C and 4D. The motion coupler (101f) can be optional when the circular belt or chain (130a) is directly coupled to the edge of the disk. In another example, the motion transfer device can comprise a rotation wheel (130b) coupled to the motion device (130) and in contact with the edge of the disk (101) so the rotation from said motion device can be transferred to said disk causing said disk to rotate (FIG. 4E), for example, the motion device can cause the rotation wheel (130b) to rotate in a wheel direction (128') causing the disk to rotate in the measuring direction (128). The devices shown in FIG. 4D and 4E can be combined with the aforementioned cup reservoir.

This disclosure is also directed to a liquid measuring system for producing one or more property values of a liquid. The liquid measuring system can comprise:

A1) the thin film device disclosed herein; and
A2) one or more measuring devices for measuring said one or more property values.

Any of the aforementioned thin film devices can be suitable for the liquid measuring system.

When in operation, the disk can be rotated by the motion device at a preset rotation speed and direction. The liquid in the first reservoir (102a) that is in contact with the disk can move along with the disk (FIG. 2A-2B). The surface of the disk can be selected based on the liquid to be measured so that the liquid can coat the surface evenly under the rotating conditions. The thin film setting edge can limit the amount or volume of the liquid that can pass the distance between the thin film setting edge and the planar first surface so a thin film (102) can be formed on the planar first surface. Excess liquid (102b) can be removed from the planar first surface by the thin film setting edge, collected and returned to the first reservoir (124) (FIG. 2A) or the cup reservoir (124') (FIG. 2B) by the liquid return channel by gravity. Any liquid that is spun off or splashed off the disk can be collected by the retainer (122) and returned to the second reservoir (123) (FIG. 2A), when present. The disk can be rotating at a measuring direction (128) (FIG. 3A-3B) such that the liquid is first going through a first point (132) that is aligned with the thin film setting edge, then through the top point (101c) of the disk, then through a second point (133) that is downstream of the top point (101c) and before the first reservoir.

The thin film formed in the area defined by the first point (132), the top point (101c) and the second point (133) can be suitable for measuring properties of the liquid and is herein referred to as "specimen measuring area". With an appropriate rotation speed and amount of the liquid in the first reservoir, the thin film (102) in the specimen measuring area can be of essentially uniform thickness. By "essentially uniform thickness", the thin film can have minor variations in thickness, such as in a range of from about 0 to about 20%, percentage based on the average thickness of the thin film. Wet film thickness can be measured using methods or devices known to those skilled in the art.

The one or more measuring devices can comprise a color measuring device (113) for measuring specimen color data of a specimen of said liquid, and optionally, an appearance measuring device for measuring specimen appearance data of said specimen (FIG. 5A and 5B). The one or more measuring devices can be coupled to the device frame with a measurement coupling (113a) that can be adjusted to position the measuring device at appropriate position and distance relative to the thin film, typically within the specimen measuring area. The measurement coupling (113a) can be coupled to the device frame via a measuring coupling (113b) (FIG. 4A-4B).

The one or more measuring devices can comprise a sparkle measuring device (141), a hiding measuring device (142), or a combination thereof. The liquid measuring system can further comprise a film thickness measuring device for measuring the thickness of the thin film. Other measuring devices that are determined suitable or developed by those skilled in the art for measuring the thin film can also be suitable.

The one or more measuring devices can be configured to have individual measuring devices positioned in pre-determined locations or groupings. In one example, a color measuring device (113), an appearance measuring device (140), a sparkle measuring device (141) and a hiding measuring device (142) can be configured as a group (FIG. 5A). The one or more measuring devices can also be configured to have one single device (113') with one or more measuring functions (FIG. 5B). Color measuring devices such as a colorimeter, a spectrophotometer, a goniospectrophotometer, or a combination thereof, can be suitable. Any suitable colorimeter or spectrophotometer, such as Model SP64 manufactured by X-Rite, Grandville, Mich., can be used. A goniospectrophotometer is also known as multi-angle spectrophotometer. Any suitable Goniospectrophotometers, such as Model MA68II from X-Rite, Grandville, Mich., or the ones provided by Murakami Color Research Laboratory, Tokyo, Japan, or by IsoColor Inc., Carlstadt, N.J., USA, can be used. Commercial instruments, such as BYK-mac available from BYK-Gardner USA, Columbia, Md., USA, that can measure color and sparkle, can also be suitable.

At least one of the measuring devices can comprise one or more illumination devices (111), such as one or more light sources, that can provide illumination to the thin film and one or more detection devices (112) (FIG. 6A-6B) that can detect reflection or spectrum of the illumination that is reflected, deflected, absorbed, or a combination thereof, by the thin film of the liquid at one or more pre-set viewing angles. A standard procedure can include ones described in ASTM E-2194, herein incorporated in by reference. The illumination devices can be configured to provide illumination at one or more pre-set illumination angles, one or more pre-determined intensities, or a combination thereof. The one or more illumination devices can also provide defused illumination at one or more pre-determined intensities. The one or more illumination devices and the one or more detection devices can positioned at the same side (FIG. 6A) or different sides (FIG. 6B) of the disk. When the illumination devices and the detection devices are positioned at different sides of the disk, a transparent disk can preferred or required.

The disk can have a hiding pattern affixed or embedded on the planar first surface. In one example, the disk can have a dark portion (150) and a light portion (151). In one example, a disk (101) having a black-and-white pattern, such as a pattern of half black (150) and half white (151), can be used (FIG. 7). The measuring devices can take measurements synchronized with the motion device so measurements from the dark portion and the light portion can be recorded, respectively. In another example, hiding power of a coating composition can be measured using color measuring device or a specific hiding measuring device to measure reflections of a thin film of the coating composition at the dark portion and the light portion, respectively. Hiding data value of the coating composition can be generated based on the ratio of the reflections at the dark and the light portions or a color difference measured over the black and white backgrounds. The color difference can be calculated using color difference calculation methods selected from $\Delta E$, $\Delta E^*_{ab}$, $\Delta E^*_{94}$, or other color difference definitions or equations, such as the color differences ($\Delta E$) based on BFD, CMC, CIE 1976, CIE 2000 (also referred to as CIEDE 2000), or any other color difference definitions or equations known to or developed by those skilled in the art. The hiding data can comprise film thickness data.

Figure 8:
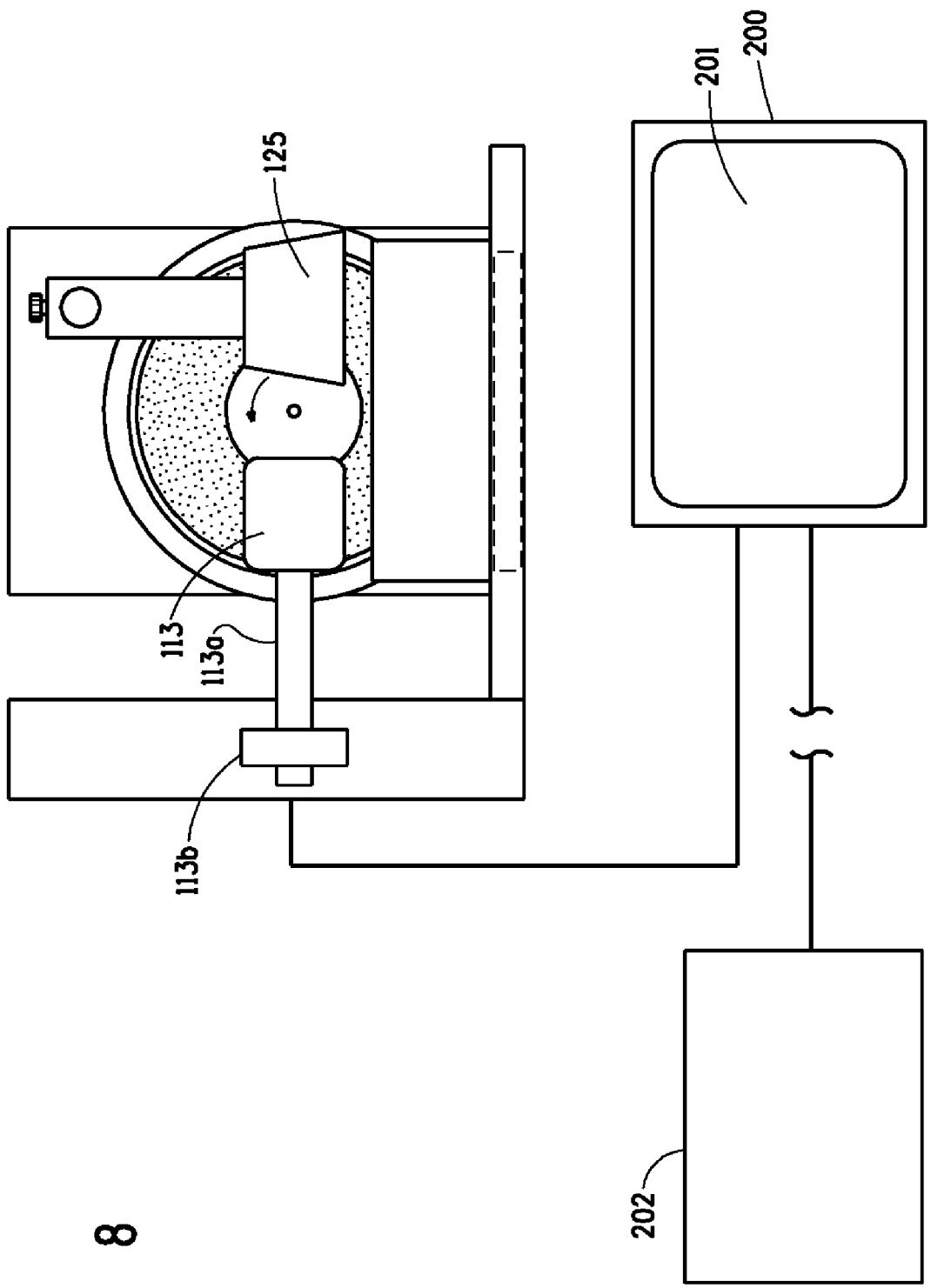
FIG. 8 shows a diagram of an example of the system.

The liquid measuring system can further comprise a computing device (200) (FIG. 8) coupled to the color measuring device, optionally the motion device, and the appearance measuring device when present. The computing device can also be coupled to other measuring devices described above, such as the sparkle measuring device, the hiding measuring device, the film thickness measuring device, or a combination thereof. Any of the aforementioned computing devices can be suitable. A portable computing device can be preferred.

The computing device can comprise a display device (201). Typical display devices, such as a monitor, a TV, a high definition monitor, a touch screen, a HDR (high dynamic range) display, an LCD display screen, a plasma display screen, an LED display screen, a projector, a printer, or a combination thereof, can be suitable. The computing device can comprise one or more display devices. The computing device and the display device can be a single device, such as a laptop computer or tablet computer, separate devices coupled via wired or wireless connections, such as a laptop with a wired or wireless display connections, for example Push2TV™ from NETGEAR® under trademark or registered trademark from NETGEAR Inc., San Jose, Calif. 95134-1911, or a combination thereof The liquid measuring system can further comprise a computing program product functionally coupled to the computing device. The computing program product can comprise computing program codes for:

1) receiving said specimen color data from the color measuring device;

2) optionally, receiving said specimen appearance data from said appearance measuring device when present;

3) generating specimen display data based on said specimen color data and optionally said specimen appearance data; and 4) displaying said specimen display data on said display device.

The computing program product can be installed on the computing device or installed on a network storage device and accessed from the computing device via wired or wireless connections. The computing program product can also be produced as a stand-alone product, such as a CD, DVD, a flash memory device comprising the computing program codes in a form that is readable or executable by a computing device.

The specimen display data can comprise R,G,B color data based on said specimen color data and optionally said specimen appearance data. Typically, R,G,B color data can be used for displaying digital image of colors or images on a digital display devices, such as aforementioned monitor, TV, high definition monitor, touch screen, HDR (high dynamic range) display, LCD display screen, plasma display screen, LED display screen, or projector. The specimen display data can be displayed as solid color images, realistic images, HDR (high dynamic range) images, realistic images rendered with BRDF (bidirectional reflectance distribution function), or a combination thereof, based on the specimen color data and optionally the specimen appearance data. The specimen display data can also be displayed as graphs, such as reflectance curves, spectral curves, numbers, or a combination thereof The liquid measuring system can further comprise a database (202). The database can be installed on the computing device, a data storage device accessible to the computing device, or a combination thereof. The database can be stored on a CD, DVD, flash memory device, a hard drive, a network drive, or a combination thereof. The database can be coupled to, or accessed from, the computing device via wired or wireless connections.

This disclosure is further directed to a system for producing a liquid composition. The system can comprise any of the aforementioned liquid measuring system. In one example, the liquid composition can be a coating composition and the system can be a coating composition production system. The coating composition can be an original equipment manufacturer (OEM) vehicle coating, or a vehicle refinish coating. Wet properties of a coating composition, such as wet color, appearance, sparkle, hiding, or a combination thereof, can be produced using the aforementioned liquid measuring system to ensure the liquid composition can be produced with desired properties.

This disclosure is further directed to a kit for assembling into a thin film device. The kit can comprise:

(a) a disk (101) comprising a planar first surface (101*a*) and a second disk surface (101*b*) on the opposite sides of said disk, and a rotation shaft (120) connectable to said disk aligned with a rotational axis (110) of the disk perpendicular to the disk surfaces for providing rotation to the disk;

(b) a device frame (121) connectable to said rotation shaft for positioning said disk and said rotation shaft;

(c) a thickness control device (125) comprising a thin film setting edge (125*a*) coupled to a liquid return channel (125*b*) and at least one frame connector (125*c*) for coupling said thin film setting edge (125*a*) and said liquid return channel (125*b*) to said device frame (121), said frame connector is connectable to said device frame and movable in respect to said device frame; and (d) a motion device (130) for providing rotation to the rotation shaft (120) and a motion control device (131) for controlling rotation speed, rotation direction, or a combination thereof, of said motion device, said motion device is connectable to said rotation shaft;

when assembled, said thickness control device (125) and said planar first surface (101*a*) are positioned at the same side of said disk (101), said thin film setting edge (125*a*) is substantially parallel to said planar first surface, and said thin film setting edge (125*a*) overlaps with said disk covering in a range of from about 50% to about 99% of the radius of said disk (101); and the distance (127) between said thin film setting edge (125*a*) and said planar first surface (101*a*) is in a range of from about 0.05 mm to about 5 mm and adjustable via said frame connector.

In another example, the kit can comprise:

(a) a disk (101) comprising a planar first surface (101*a*) and a second disk surface (101*b*) on the opposite sides of said disk, and a rotation shaft (120) connectable to said disk aligned with a rotational axis (110) of the disk perpendicular to the planar first surface allowing rotation of the disk along said rotational axis (110), at least a circular portion (101*e*) of said planar first surface is rotationally symmetric to said rotational axis;

(b) a device frame (121) connectable to said rotation shaft for positioning said disk and said rotation shaft;

(c) a thickness control device (125) comprising a thin film setting edge (125*a*) coupled to a liquid return channel (125*b*) and at least one frame connector (125*c*) for coupling said thin film setting edge (125*a*) and said liquid return channel (125*b*) to said device frame (121), said frame connector is connectable to said device frame and movable in respect to said device frame; and (d) a motion device (130) for providing rotation to the disk, and a motion control device (131) for controlling rotation speed, rotation direction, or a combination thereof, of said motion device, said motion device is connectable to said disk;

when assembled, said thickness control device (125) and said planar first surface (101*a*) are positioned at the same side of said disk (101), and said thin film setting edge (125*a*) is substantially parallel to said planar first surface; and the distance (127) between said thin film setting edge (125*a*) and said planar first surface (101*a*), when assembled, is in a range of from about 0.05 mm to about 5 mm and adjustable via said frame connector.

The kit can further comprise a first reservoir (124) for storing said liquid. The kit can further comprise a second reservoir (123) and a retainer (122), said second reservoir can be connectable to the device frame and can be so positioned to collect overflow of the liquid, when present, retained by said retainer, when assembled.

The disk (101) can further comprise a circular retaining barrier (129) positioned at the circular edge of said disk.

The kit can further comprise a color measuring device, an appearance measuring device, a sparkle measuring device, a hiding measuring device, or a combination thereof The length (125*d*) of said thin film setting edge (125*a*) can be in a range of from about 50% to about 99% of the radius (101*d*) of said disk.

This disclosure is further directed to a process for producing one or more property values of a liquid. The process can comprise the steps of:

C1) producing a thin film of a specimen of the liquid at a predetermined film thickness in a range of from about 0.05 mm to about 2 mm using a thin film device comprising:

(a) a disk (101) comprising a planar first surface (101*a*) and a second disk surface (101*b*) on the opposite sides of said disk, said disk is coupled to a rotation shaft (120) aligned with the rotational axis (110) of the disk perpendicular to the disk surfaces for providing rotation to the disk;

(b) a device frame (121) that positions said disk and said rotation shaft;

(c) a thickness control device (125) comprising a thin film setting edge (125*a*) coupled to a liquid return channel (125*b*) and at least one frame connector (125*c*) coupling said thin film setting edge (125*a*) and said liquid return channel (125*b*) to said device frame (121), said frame connector is movable in respect to said device frame; and (d) a motion device (130) coupled to said rotation shaft for providing rotation to the rotation shaft (120), and a motion control device (131) for controlling rotation speed, rotation direction, or a combination thereof, of said motion device;

wherein said thickness control device (125) is positioned at said planar first surface (101*a*) side of said disk (101), said thin film setting edge (125*a*) is substantially parallel to said planar first surface, and said thin film setting edge (125*a*) overlaps with said disk covering in a range of from about 50% to about 99% of the radius of said disk (101);

wherein the distance (127) between said thin film setting edge (125*a*) and said planar first surface (101*a*) is in a range of from about 0.05 mm to about 5 mm and adjustable via said frame connector; and wherein said predetermined film thickness is controlled by said distance (127) and the rotation speed and direction;

C2) measuring said thin film with one or more measuring devices to produce specimen data; and C3) producing said one or more property values based on said specimen data.

In the aforementioned process, the thin film can be produced by a thin film process comprising the steps of:

C1a) depositing the specimen of the liquid on a portion of the planar first surface; and C1b) rotating the disk to form the thin film (102) on the planar first surface;

wherein the disk is rotating at a speed allowing said liquid to spread over said planar first surface, but not spinning off said disk.

The specimen can be deposited onto the planar first surface before the disk starting to spin or while it is spinning.

The thin film device can further comprise a first reservoir (124) for storing said liquid (102*a*), and at least a portion of said disk is in contact with the liquid stored in said first reservoir.

The disk can be rotating at a direction so that the liquid is moved by the disk from the first reservoir to the thin film setting edge against gravity to form the think film on said planar first surface. Any overflow liquid, when present, can be removed from the planar first surface by the thin film setting edge, collected and returned to the first reservoir by said liquid return channel by gravity.

The one or more measuring devices comprise a color measuring device, and optionally, an appearance measuring device.

Figure 4E:
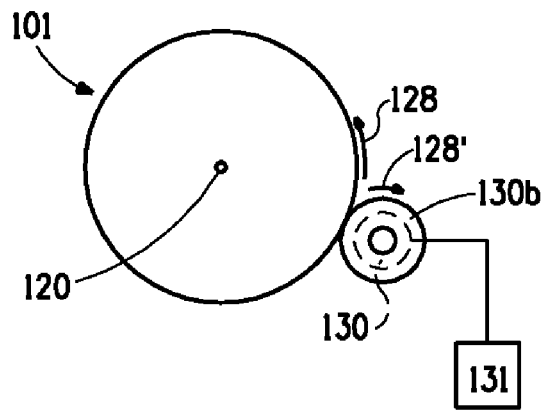

For the entire disclosure herein, the motion control device (131) can be positioned near or on the device frame, such as shown at least in FIG. 1A-1B and FIG. 2A-2C, or remotely, such as shown in FIG. 4C-4E. The motion control device can also be connected to the motion device via wired or wireless connections.

The one or more property values can comprise specimen color data and optionally specimen appearance data measured from the specimen of said liquid, said specimen color data can be selected from specimen color reflection data, specimen color spectral data, specimen color data derived from said specimen color reflection data, specimen color data derived from said specimen color spectral data, or a combination thereof. Property data for the wet liquid (wet data) and after the liquid is dry (dry data) can be converted, correlated, or otherwise related by testing, mathematical modeling, or a combination thereof. In one example, the one or more property values can comprise wet color data, dry color data derived from the wet color data, wet hiding data, dry hiding data derived from the wet hiding data, wet appearance data, dry appearance data derived from the wet appearance data, or a combination thereof The process can further comprise the steps of:

D1) generating from a computing device (200) specimen display data based on said specimen color data and optionally said specimen appearance data; and D2) displaying said specimen display data on a display device (201) coupled to said computing device.

The specimen display data can comprise R,G,B color data based on said specimen color data and optionally said specimen appearance data.

The color measuring device, optionally, the appearance measuring device, can be positioned at the planar first surface distal to said liquid returning channel for measuring the thin film on the planar first surface.

The process can further comprise the step of adjusting the distance between said color measuring device (113), optionally, said appearance measuring device (140), and said planar first surface.

The thin film device can further comprise a second reservoir (123) and a retainer (122), said second reservoir is positioned to collect overflow of said liquid, when present, retained by said retainer.

The disk (101) can further comprise a circular retaining barrier (129) positioned at the circular edge of said disk.

The length (125d) of said thin film setting edge (125a) can be in a range of from about 50% to about 99% of the radius (101d) of said disk.

The one or more measuring devices can comprise a sparkle measuring device (141), a hiding measuring device (142), or a combination thereof The thin film thickness can be in a range of from about 0.05 mm to about 0.8 mm.

The process can further comprise the step of:

C4) storing said one or more property values, said specimen data, or a combination thereof, in a database (202).

The specimen data can be produced by measuring the thin film with one or more measuring devices simultaneously or sequentially. The specimen data can be produced by measuring the thin film with one or more measuring devices at a same portion or different portions of said thin film. In one example, the color and appearance specimen data can be measured at the same portion of the thin film. In another example, the color specimen data, appearance specimen data, the hiding specimen data, can be measured at different portions of the thin film.

The liquid can be a coating composition.

Advantages of this disclosure can include better film thickness control, especially for low viscosity liquid. Further advantage can include that the device can be easily cleaned since any liquid spun off or dripping off the disk can be collected.

Although the thin film device, the liquid measuring system and the process disclosed herein are specifically disclosed as suitable for producing coating compositions, they can be suitable for producing liquid that one or more properties are to be controlled or monitored. The liquid can include, for example, inks, dyes, beverages, or any other liquid for consumer use or industrial applications.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration in any way. Rather, the foregoing detailed description will provide those skilled in the art with a convenient road map for implementing an exemplary embodiment, it being understood that various changes may be made in the function and arrangement of elements described in an exemplary embodiment without departing from the scope as set forth in the appended claims and their legal equivalents.

What is claimed is:

1. A thin film device for producing a thin film of a liquid, said thin film device comprising:
   a disk comprising a planar first surface and a second disk surface on the two opposite sides of said disk, wherein said disk is coupled to a rotation shaft that is aligned with a rotational axis of said disk perpendicular to the planar first surface allowing rotation of the disk along said rotational axis, and wherein at least a circular portion of said planar first surface is rotationally symmetric to said rotational axis;
   a device frame that positions said rotation shaft and said disk;
   a thickness control device comprising a thin film setting edge coupled to a liquid return channel and at least one frame connector coupling said thin film setting edge and said liquid return channel to said device frame, wherein said frame connector is movable in respect to said device frame; and
   a motion device coupled to said disk for providing rotation to the disk, and a motion control device for controlling rotation speed, rotation direction, or a combination thereof, of said motion device;
   wherein said thickness control device is positioned at said planar first surface side of said disk, and said thin film setting edge is substantially parallel to said planar first surface; and
   wherein the distance between said thin film setting edge and said planar first surface is in a range of from about 0.05 mm to about 5 mm and adjustable via said frame connector.

2. The thin film device of claim 1, further comprising a first reservoir for storing said liquid, wherein said first reservoir is configured so that said liquid, when present in said first reservoir, is in contact with at least a portion of said planar first surface.

3. The thin film device of claim 1, further comprising a second reservoir and a retainer, wherein said second reservoir is positioned to collect overflow of said liquid, when present, retained by said retainer.

4. The thin film device of claim 1, wherein said disk is a circular disk and further comprises a circular retaining barrier positioned at the circular edge of said disk.

5. The thin film device of claim 1, wherein said disk is so positioned that said liquid, when present, is moved by said disk, when in rotation, from said first reservoir to said thin film setting edge against gravity.

6. The thin film device of claim 1, wherein the length of said thin film setting edge is in a range of from about 50% to about 99% of the radius of said disk.

7. The thin film device of claim 1, wherein said second disk surface is a non-planar surface.

8. The thin film device of claim 1, wherein said motion device is coupled to said disk by directly coupling to said rotation shaft, via a motion transfer device, or a combination thereof.

9. A liquid measuring system for producing one or more property values of a liquid, said liquid measuring system comprising:
a thin film device, wherein said thin film device comprises:
a disk comprising a planar first surface and a second disk surface on the two opposite sides of said disk, wherein said disk is coupled to a rotation shaft that is aligned with a rotational axis of said disk perpendicular to the planar first surface allowing rotation of the disk along said rotational axis, and wherein at least a circular portion of said planar first surface is rotationally symmetric to said rotational axis;
a device frame that positions said rotation shaft and said disk;
a thickness control device comprising a thin film setting edge coupled to a liquid return channel and at least one frame connector coupling said thin film setting edge and said liquid return channel to said device frame, wherein said frame connector is movable in respect to said device frame; and
a motion device coupled to said disk for providing rotation to the disk, and a motion control device or controlling rotation speed, rotation direction, or a combination thereof, of said motion device;
wherein said thickness control device is positioned at said planar first surface side of said disk, and said thin film setting edge is substantially parallel to said planar first surface; and
wherein the distance between said thin film setting edge and said planar first surface is in a range of from about 0.05 mm to about 5 mm and adjustable via said frame connector; and
one or more measuring devices for measuring said one or more property values.

10. The liquid measuring system of claim 9, wherein said thin film device further comprises a first reservoir for storing said liquid, wherein said first reservoir is configured so that said liquid, when present in said first reservoir, is in contact with at least a portion of said planar first surface.

11. The liquid measuring system of claim 9, wherein said thin film device further comprises a second reservoir and a retainer, wherein said second reservoir is positioned to collect overflow of said liquid, when present, retained by said retainer.

12. The liquid measuring system of claim 9, wherein said disk is a circular disk and further comprises a circular retaining barrier positioned at the edge of said disk.

13. The liquid measuring system of claim 9, wherein said disk is so positioned that said liquid, when present, is moved by said disk, when in rotation, from said first reservoir to said thin film setting edge against gravity, and wherein the length of said thin film setting edge is in a range of from about 50% to about 99% of the radius of said disk.

14. The liquid measuring system of claim 9, wherein said one or more measuring devices comprise a color measuring device for measuring specimen color data of a specimen of said liquid, and optionally, an appearance measuring device for measuring specimen appearance data of said specimen.

15. The liquid measuring system of claim 14, further comprising a computing device coupled to said color measuring device, optionally said motion device, and said appearance measuring device when present.

16. The liquid measuring system of claim 15, wherein said computing device comprises a display device.

17. The liquid measuring system of claim 16, further comprising a computing program product functionally coupled to said computing device, wherein said computing program product comprises computing program codes for:
receiving said specimen color data from said color measuring device;
optionally, receiving said specimen appearance data from said appearance measuring device when present;
generating specimen display data based on said specimen color data and optionally said specimen appearance data; and
displaying said specimen display data on said display device.

18. The liquid measuring system of claim 17, wherein said specimen display data comprise R,G,B color data based on said specimen color data and optionally said specimen appearance data.

19. The liquid measuring system of claim 9, wherein said one or more measuring devices comprise a sparkle measuring device, a hiding measuring device, or a combination thereon.

20. A kit for assembling into a thin film device, said kit comprising:
a disk comprising a planar first surface and a second disk surface on the opposite sides of said disk, and a rotation shaft connectable to said disk aligned with a rotational axis of the disk perpendicular to the planar first surface allowing rotation of the disk along said rotational axis, wherein at least a circular portion of said planar first surface is rotationally symmetric to said rotational axis;
a device frame connectable to said rotation shaft for positioning said disk and said rotation shaft;
a thickness control device comprising a thin film setting edge—coupled to a liquid return channel and at least one frame connector for coupling said thin film setting edge and said liquid return channel to said device frame, wherein said frame connector is connectable to said device frame and movable in respect to said device frame; and
a motion device for providing rotation to the disk, and a motion control device for controlling rotation speed, rotation direction, or a combination thereof, of said motion device, wherein said motion device is connectable to said disk;
wherein when assembled, said thickness control device and said planar first surface are positioned at the same side of said disk, and said thin film setting edge is substantially parallel to said planar first surface; and wherein the distance between said thin film setting edge and said planar first surface, when assembled, is in a range of from about 0.05 mm to about 5 mm and adjustable via said frame connector.

* * * * *